United States Patent [19]
Yerfino et al.

[11] Patent Number: 6,017,325
[45] Date of Patent: Jan. 25, 2000

[54] DISPOSABLE SYRINGE WITH AUTOMATICALLY RETRACTABLE HYPODERMIC NEEDLE

[76] Inventors: Daniel Alberto Yerfino, Esquiú 863, (7600), Mar del Plata; Aldo Luis Ducler, Corrientes 415, 6° Floor, Buenos Aires, both of Argentina

[21] Appl. No.: 09/082,536
[22] Filed: May 21, 1998
[51] Int. Cl.⁷ ..................................................... A61M 5/00
[52] U.S. Cl. ........................ 604/110; 604/218; 604/222; 604/195
[58] Field of Search ..................... 604/187, 110, 604/162, 163, 167, 171, 192, 194, 195, 197, 198, 199, 200, 201, 205, 232, 240, 263, 411–414, 228, 218, 229, 243, 221, 222, 225; 128/919

[56] References Cited

U.S. PATENT DOCUMENTS

| | | | |
|---|---|---|---|
| 4,995,874 | 2/1991 | Strickland | 604/110 |
| 5,120,310 | 6/1992 | Shaw | 604/110 |
| 5,152,750 | 10/1992 | Haining | 604/195 |
| 5,180,370 | 1/1993 | Gillespie | 604/110 |
| 5,181,912 | 1/1993 | Hammett | 604/228 |
| 5,190,526 | 3/1993 | Murray et al. | 604/110 |
| 5,222,944 | 6/1993 | Harris | 604/110 |
| 5,267,961 | 12/1993 | Shaw | 604/195 |
| 5,308,329 | 5/1994 | Mazur et al. | 604/110 |
| 5,320,606 | 6/1994 | Jore | 604/110 |
| 5,324,265 | 6/1994 | Murray et al. | 604/110 |
| 5,382,235 | 1/1995 | Sak | 604/110 |
| 5,458,576 | 10/1995 | Haber et al. | 604/110 |
| 5,578,015 | 11/1996 | Robb | 604/195 |
| 5,616,134 | 4/1997 | Firth et al. | 604/192 |
| 5,656,031 | 8/1997 | Thorne et al. | 604/110 |

FOREIGN PATENT DOCUMENTS

| | | | |
|---|---|---|---|
| WO 89/10151 | 11/1989 | WIPO | 604/110 |

*Primary Examiner*—Wynn Wood Coggins
*Assistant Examiner*—Sharon Finkel
*Attorney, Agent, or Firm*—Finnegan, Henderson, Farabow, Garrett & Dunner, L.L.P.

[57] ABSTRACT

A disposable syringe with an automatically retractable hypodermic needle for use in the injection of medicinal substances and/or the removal or samples of blood and liquids in general in human or veterinary medicine is disclosed. Once the operation of the syringe is performed the application of slight additional pressure to the end of the piston's travel causes the needle to be automatically shot inwards, with it remaining permanently housed in the interior in order to protect the operator from pricks or contact with pathogenic substances, and also making it unusable for subsequent applications.

11 Claims, 4 Drawing Sheets

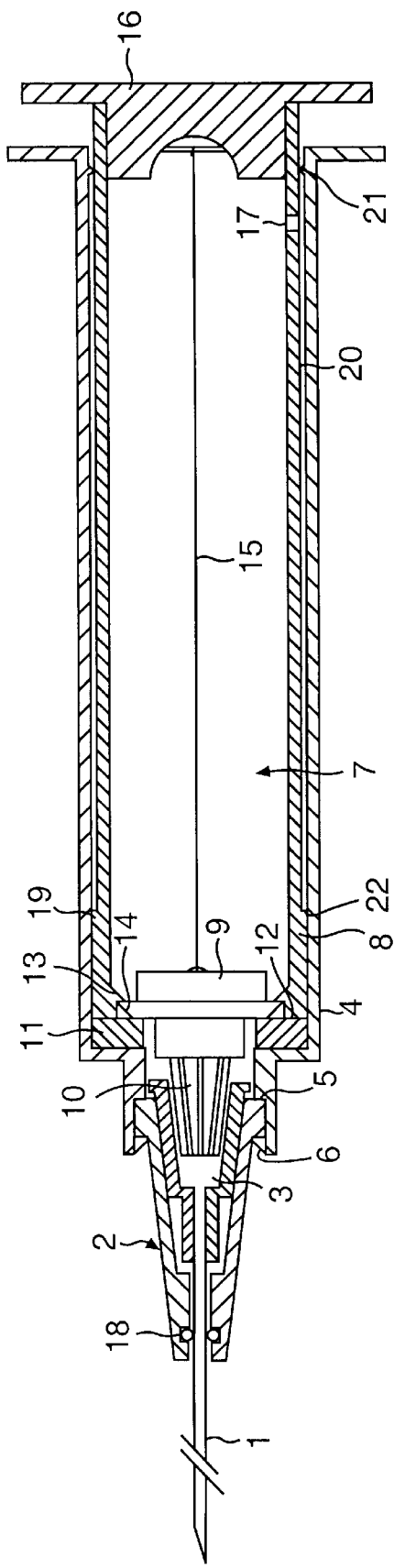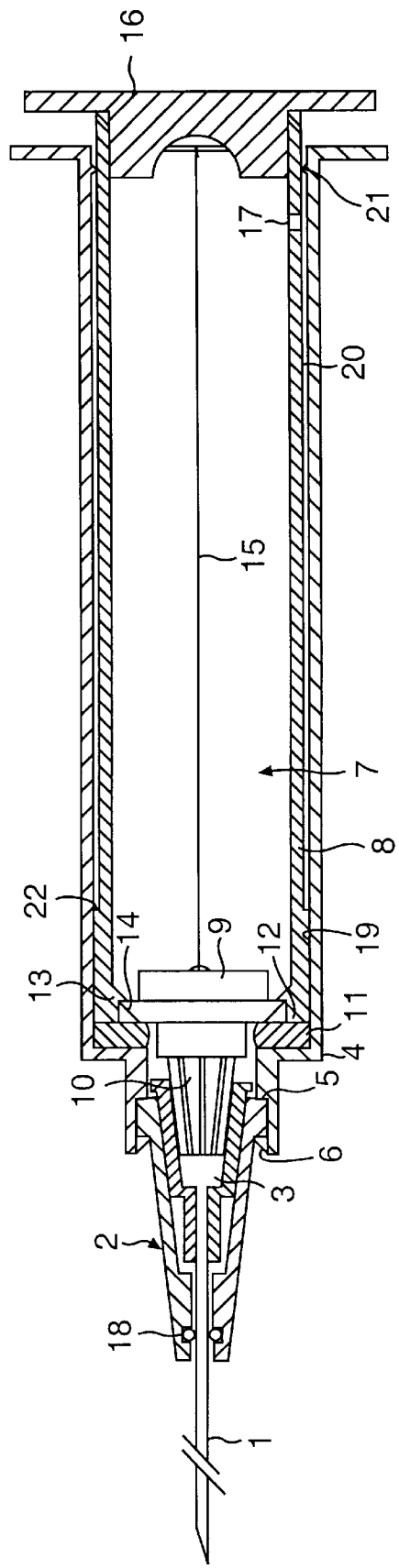

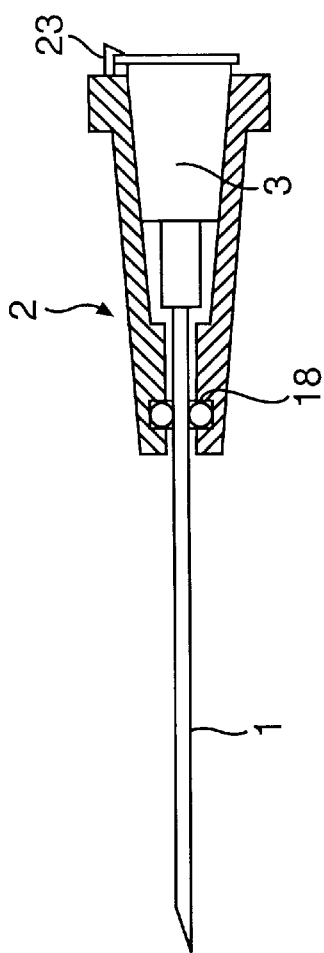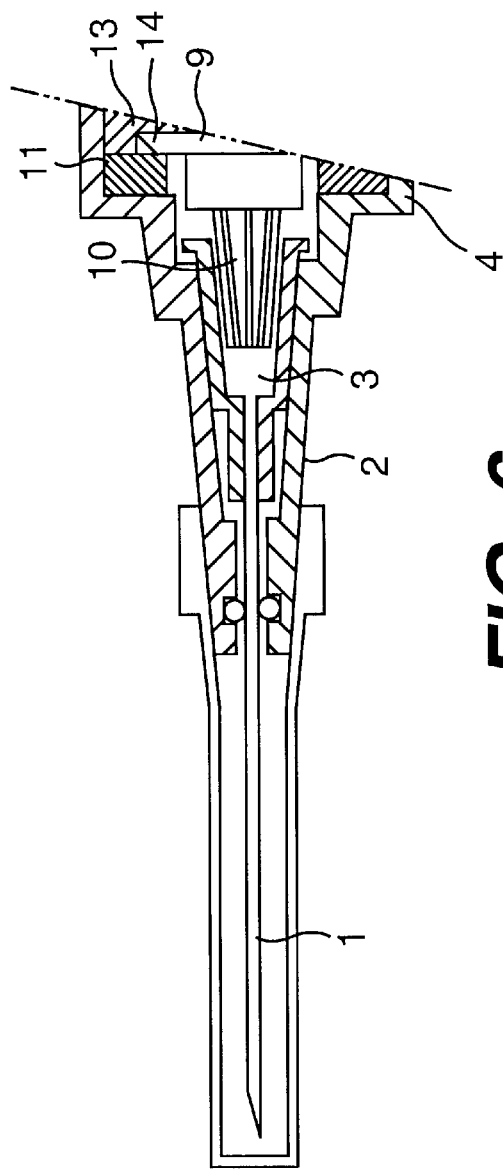

DISPOSABLE SYRINGE WITH AUTOMATICALLY RETRACTABLE HYPODERMIC NEEDLE

BACKGROUND OF THE INVENTION

1. Field of the Invention

This invention relates to a disposable syringe with automatically retractable hypodermic needle, for use in the injection of medicinal substances and/or the removal of samples of blood and liquids in general in human or veterinary medicine, with the special feature that once the operation is performed the application of slight additional pressure to the end of the piston's travel causes the needle to be automatically shot inwards, with it remaining permanently housed in the interior in order to protect the operator from pricks or contact with pathogenic substances, and also making it unusable for subsequent applications.

2. Description of the Related Art

In the procedures mentioned hypodermic needles are normally fitted to syringes and represent a great hazard of infection to those persons responsible for their subsequent handling, not only because of their ability to prick, but also because they retain contaminating residues. In order to protect operating personnel from these risks, in practice containers are used which are designed to capture and store these units, which are then transported to incinerators for total destruction. However these operations are risky because disposal does not take place immediately, especially in operating theaters in which the operating surgeon's attention is concentrated on the operating field, and little attention is involuntarily paid to the disposal of such units once used. On the other hand, those responsible for removing the containers mentioned are exposed to accidents given that the uncovered needles can pass through their walls and the operation of placing them in a protective cap represents an additional risk.

There is also the possibility that someone committing a fraudulent act might reuse the syringes disposed of, causing severe harm to subsequent patients.

Various types of hypodermic syringes with a retractable needle which are intended to overcome the disadvantages described, which have a functional behavior which differs from that described herein, are known. Nevertheless those which are most widely known will be mentioned above, pointing out their obvious differences.

These are U.S Pat. Nos. 5,152,750, 5,180,370, 5,222,944, 5,382,235, 5,578,015 and 5,616,134, which form a group with nonautomatic retraction. U.S. Pat. No. 5,190,526, which requires great complexity in fitting of the piston, given that this must disassemble, in order to break, into a plug which is retained at the working front and a retracting capture unit, with the disadvantage that there is no possibility of fitting and removing the needle from the exterior, nor of retaining the residual liquids which normally remain at said front; on the other hand the needle used has to be manufactured specially only for this mechanism. U.S. Pat. No. 5,324,265, which is merely an improvement on the above, which converts it into a syringe with an externally removable needle, but retains the other disadvantages mentioned. U.S. Pat. No. 5,320,606, in which the member acting as a piston slides externally until its edge produces an opening for a seal which holds the needle-holding tip in position, which is integral with an elastomer member which controls the passage of liquids; the elastic condition required of this tubular member represents a construction problem in the region in which it is incorporated with the needle holder and, at its other end, with the end of the tube containing it; furthermore, the positioning of the fin for fixing this syringe, which is so close to its working front, makes it inconvenient to handle. U.S. Pat. No. 5,656,031, which has a breaking and retraction mechanism initiated by the pusher of an external protector, which gives rise to risks in application and our U.S. application Ser. No. 09/005681, which is fundamentally distinguished by the manner in which it captures the needle and its capturing mechanism, which does not permit the option of external mounting.

SUMMARY OF THE INVENTION

This invention is intended to go beyond the design of those mentioned, providing greater constructional simplicity and functional efficiency.

In particular, it relates to a syringe comprising a hollow tube within which the corresponding piston slides tightly, equipped respectively with posterior fins which receive and spread the external push as in conventional syringes. The hollow tube mentioned has a cylindrical mouth at its operating end with an internal annular step and elastic retaining tongues arranged internally in the vicinity of the edge thereof, forming a housing which is capable of supporting a needle for injection and extraction. This latter component, which is incorporated with the whole, is a tubular body with a posterior widening forming a cylindrical section which is introduced into the housing mentioned above, overcoming the elasticity of the tongues and abutting against the annular step in order finally to be retained by the return of the latter to their initial position. At its posterior opening the needle holder has an axial frustoconical cavity which coincides with the external shape of the coupling nipple of a standard needle which is extended to its end in a cylindrical duct, guiding the needle tube, positioned with said coupling nipple wedged in the space mentioned. For its part the duct described has a transverse seal of absorbent elastic material through which the needle tube passes, which is capable of absorbing liquids from its outer surface and closing it off when it is retracted. The difference in surface area between the cross section of the hollow tube and the cylindrical mouth holding the needle holder gives rise to a first front wall against which there is fitted internally an elastomer washer placed between it and the end of the piston. The latter is a tube having an axially slidable front section with a leaktight fit with respect to the outer hollow tube and a reduction in the same in its posterior part to reduce friction. At the front the piston in question is blind, as a consequence of a terminal needle capture device fitted flush with its front edge and held from a sealing perimeter projection by elastic tongues within it. Up to the working end the capture device mentioned extends as a frustoconical tip equivalent to the internal empty volume of the coupling nipple of the needle, against which it abuts axially, being linked by its rear face to the base of the piston by elastic means which is under tension in its original position.

The base of the piston is closed off by an integral plug which with its peripheral outer widening forms the pushing means. To complete the description of the construction the piston is provided with escape openings from its internal chamber in its distal portion and, without this constituting an excluding condition, the outer cylinder may be fitted with ends on its inner enclosing wall which prevent rearward movement of the enclosure sealing the piston at the end of its travel, preventing it from being uncoupled on opening; longitudinal channels in the capturing tip which provide for complete drainage of the compressed liquid when this is wedged in the coupling nipple of the needle, or said channels may be made in the latter and secondary elastic catches which help to hold the needle in the needle holder.

The assembly described is presented for use with the hypodermic needle wedged in the needle holder, where it may be further retained by means of the secondary elastic tongues mentioned and is optionally mounted on or separate from the outer body of the syringe, given that the piston lies with its working front on the corresponding face of the elastomer washer with its capturing tip opposite the opening of the needle when this has been fitted, without penetrating it totally.

For taking up the injectable substance from its container or extracting biological samples the piston is moved in the same way as in known syringes, after removal of the protective cap.

To inject a medicinal substance or to place the sample extracted in laboratory test tubes the procedure is again the same as with known syringes, that is, the piston is pushed down to the end of its travel, so that its front end is again in contact with the elastomer washer. From this point access is available to operation of the novel safety device merely by exerting slightly greater pressure than that required for the previous procedure, continuously with it; this causes the elastomer washer to be flattened by the end of the piston tube until the capturing tip is introduced into the coupling nipple of the needle and becomes firmly wedged within it. As a consequence of accurate dimensioning said frustoconical tip encounters a stop to its progress. At this point the slight residual advance which the elastomer washer allows the piston tube brings about breakage of the annular projection of the capturing end with respect to the elastic tongues within it, leaving it exposed to the retractile force of the elastic medium, which pulls the needle permanently inwards, given that the firmness with which the capturing tip is wedged in the coupling nipple overcomes the relationship between the latter and the needle holder.

The retractile movement of the needle takes place linearly, until it disappears from the exterior, guided by the needle holder, and in its travel the absorbent membrane prevents residual liquid from dripping from its enclosing surface.

Without altering the functional principle described, which constitutes the present invention, the following alternative variants have been considered:

a) A syringe like that described, in which the needle is originally fitted internally, without possibility of leaving from the front, in which case the needle holder constitutes an extension which is integral with the working end of the outer tube.

b) A syringe such as that described or as described in alternative a) (both cylindrical) with the axis of the needle and its capture mechanism being displaced from the center, so that a longitudinal channel will be necessary in one of its tubular components, coinciding with an equivalent longitudinal projection in the other, acting as a guide so that said capture mechanism operates in the same line as the needle, and another similar guide means linking the inner tube with the capturing end.

c) A syringe as described or as mentioned in alternative a) having an elliptical transverse cross section and a central needle.

d) A syringe as described or as mentioned in alternative a) having an elliptical transverse cross section and a needle which is displaced from its center, coinciding with its capture mechanism.

e) A syringe as described or as mentioned in alternative b), having an anatomical cross section determined by an ellipse, with one of its major lengths transversely concave.

BRIEF DESCRIPTION OF THE DRAWINGS

To give physical form to the advantages which have been merely mentioned and in order to aid understanding of the constructional and functional features of this disposable syringe with an automatically retractable hypodermic needle, a description is provided below of a preferred embodiment and variants which are illustrated diagrammatically and without any specific scale in the appended drawing figures, with the express clarification that as this is specifically an example, no restrictive or exclusive character should be assigned to it, its purport being merely illustrative of the fundamental concept on which it is based.

FIG. 1 is a longitudinal cross section of a syringe according to the invention with an external needle in the confirmation of its original position.

FIG. 2 is a figure equivalent to the above with the piston at the end of its compression stroke.

FIG. 5 is a view equivalent to the above of a needle holder with a secondary retention catch.

FIG. 6 is a view equivalent to the above from the end of a syringe with the needle incorporated internally.

DETAILED DESCRIPTION OF THE PREFERRED EMBODIMENTS

Figure 3:
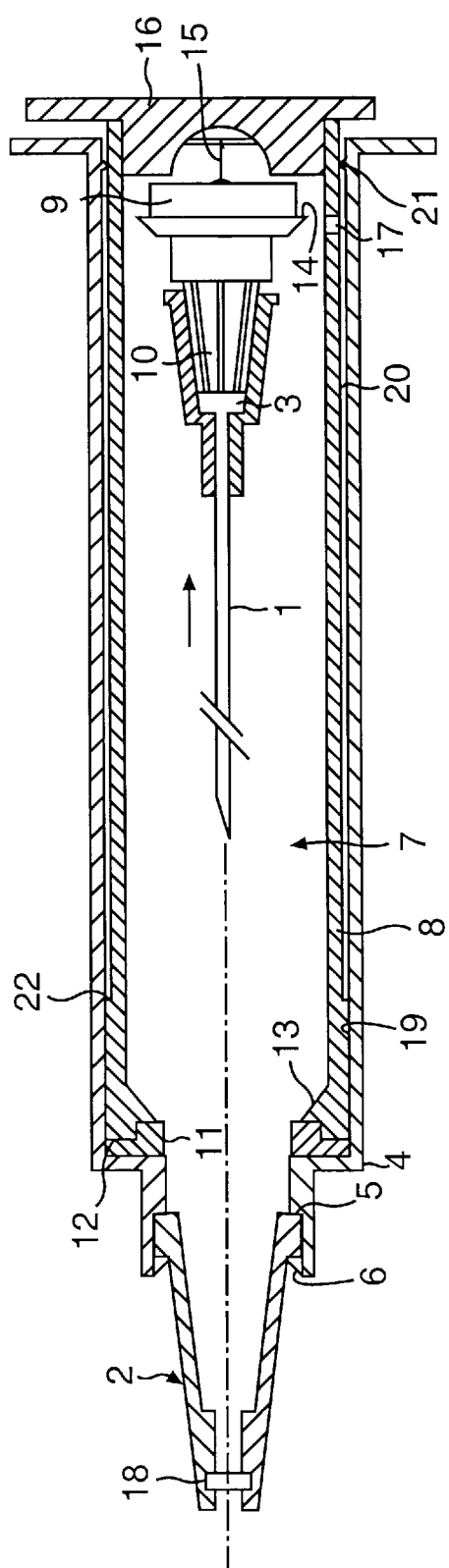
FIG. 3 is a figure equivalent to the above with excess pressure applied to the piston and the capture device and the needle retracted.

In all the figures, identical reference numbers correspond to the same or equivalent parts or structural elements of the assembly taken as an example for this explanation.

In FIG. 1, which shows a syringe for injection and extraction, it will be seen that a hypodermic needle 1 is fitted in needle holder 2 into which it is introduced through its posterior opening until it is retained by being wedged on its coupling nipple 3. This needle holder is retained in the forward housing of outer tube 4 between posterior terminal seat 5 and elastic tongues 6. Compressor piston 7 comprising inner tube 8 and outer capture device 9 with its capturing tip 10 is in this figure in unpressurized contact with elastomer washer 11 which is located between this and the front wall of said outer tube 4. Under these conditions capturing tip 10 is inserted into coupling nipple 3 but is not in contact with it.

In the following sequence, shown by FIG. 2, the piston has moved forward, slightly compressing elastomer washer 11 to a point such that it enables tip 10 to be wedged in nipple 3 with a force greater than the retaining force in needle holder 2, given the undeformability of the former and the greater roughness of its surface, which is also provided with longitudinal grooves for the complete expulsion of liquids in the final stage, although these grooves may belong to the nipple of the needle.

In FIG. 3, excess pressure has been applied to the piston, which causes final advance of front end 12, further compressing elastomer washer 11, and not capturing end 9 which has encountered a stop in its travel. For this reason, elastic tongues 13 of inner tube 8 break off perimetral projection 14 of capturing unit 9, leaving this exposed to the pull of elastic medium 15 which being anchored at the rear to plug 16 causes it to be retracted with the captured needle, while the air between them, which might impede rearward movement, escapes through orifice or orifices 17. The needle holder guide is sufficient to ensure that the needle is retracted linearly while it is present in the exterior, while absorbent member 18 cleans it avoiding any dripping of residual liquids. In the illustrations, it can be seen that the piston has a leak tight sliding head 19 and a posterior section of reduced cross section in order to reduce friction giving rise to a peripheral space 20 for the escape of air. In addition to this, the syringe illustrated in the example is equipped with a stop 21 in the interior of its outer tube, which when in contact with perimetral step 22 on the piston prevents it from any subsequent excursion when at its maximum extension.

Figure 4:
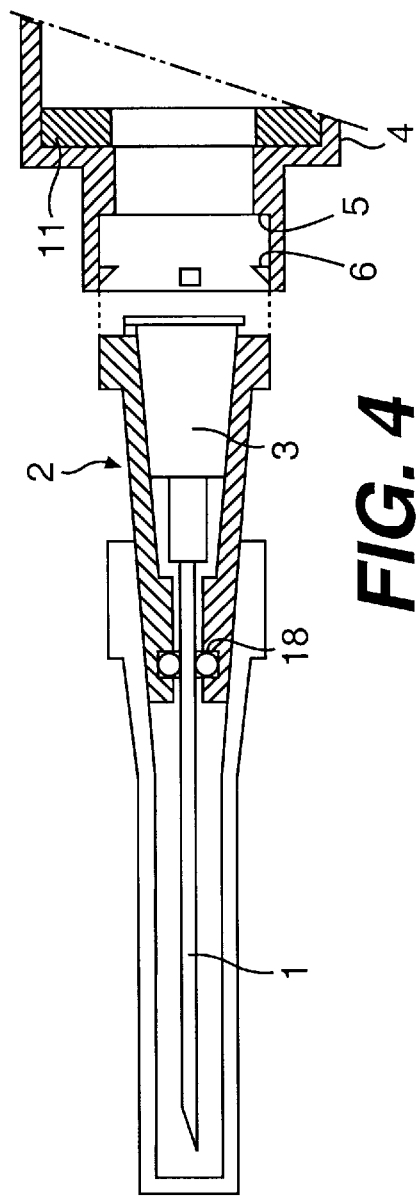
FIG. 4 is a partial cross section of a needle holder separated from the syringe.
Figure 8:
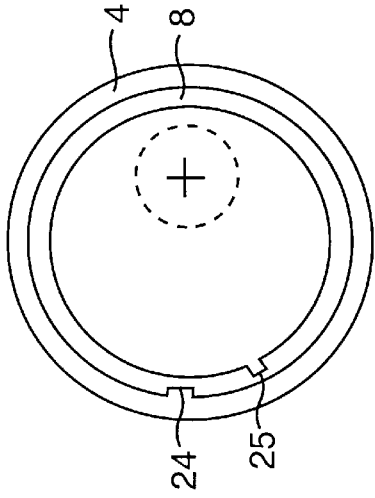
FIG. 8 is a view equivalent to the above of a cylindrical syringe with an eccentric needle.
Figure 7:
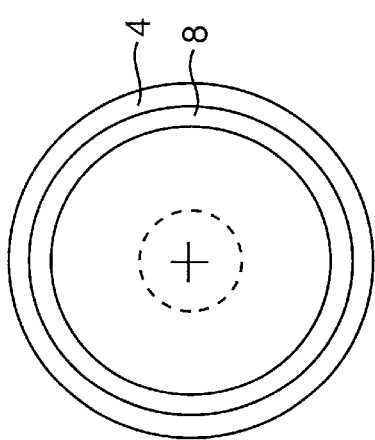
FIG. 7 is a diagrammatical representation of the transverse cross section of a cylindrical syringe with a central needle.

FIG. 4 shows a needle holder 2 with its needle 1 fitted and a protective cap over the front opening of the syringe, in which can be seen elastic tongues 6 and its posterior stop step 5.

FIG. 5 is intended to show a posterior elastic tongue 23 in a needle holder 2, which is complementary but not essential, which is designed to retain coupling nipple 3 of needle 1.

In FIG. 6, needle holder 2 forms an integral part of extension tube 4 and belongs to a syringe with a nonretractable internal needle equipped with a protective cap.

Figure 11:
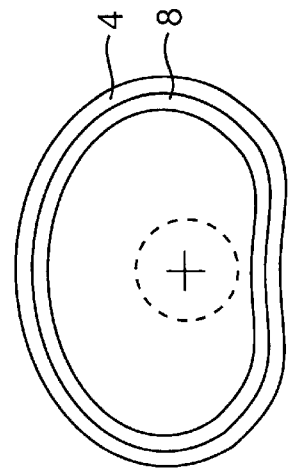
FIG. 11 is an equivalent view to the four above of a syringe having an elliptical cross section with a concave length and a central needle.
Figure 10:
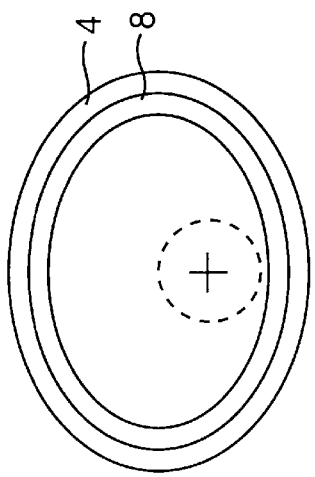
FIG. 10 is a view equivalent to the three above of a syringe with an elliptical cross section and an eccentric needle.
Figure 9:
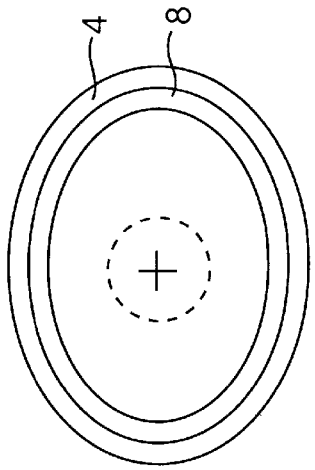
FIG. 9 is a view equivalent to the above of a syringe with an elliptical cross section and a central needle.

Finally, FIGS. 7, 8, 9, 10 and 11 show in diagrammatical form various alternative cross sections of syringes which are capable of operating using the basic principle described, selected from a large possible variety. The first of these shows a cylindrical syringe with a concentric needle; the next is a cylindrical syringe with the center of the needle displaced and a longitudinal guide 24 which prevents the piston from rotating with respect to the outer tube, given that correcting guide 25 in the capturing plug prevents it from being displaced angularly with respect to the piston; in FIG. 9 the cross section of the syringe describes an ellipse and the axis of the needle is central, for which reason it is self-centering. The following FIG. 10 shows a cross section like the former but its needle is eccentric, so that it does not need any longitudinal guide, provided that it has first been correctly assembled, and the final FIG. 11 shows a cross section of an anatomical syringe which is ideal for use almost parallel to the body surface, with its concave side supported on it to avoid lateral movements, this conformation also being self-centering.

Modifications may in practice be incorporated in the disposable syringe with an automatically retractable hypodermic needle as described and illustrated by examples which modifications must be regarded as variant embodiments lying within the scope of the protection of this patent of invention which is described in its essentials by the text of the clauses of the following claims.

We claim:

1. A disposable syringe with an automatically retractable hypodermic needle, comprising:

an outer tube having an internal diameter and a forward housing defining an inner front wall face and a coupling end, a piston in the outer tube and having a hollow tube shank, at least a posterior section of the shank having a diameter less than the internal diameter of the outer tube, and an annular working face movable toward the inner front wall face of the outer tube, a needle holder connected to the coupling end of the outer tube, the needle holder having a distal guide conduit, a hypodermic needle in the distal guide conduit of the needle holder and having a coupling nipple wedged in a posterior axial portion of the needle holder, an annular elastomer washer housed between the inner face of the front wall of the outer tube and the working face of the piston;

a plug in the annular working face of the piston, the plug having a perimetral projection caught posterially by small internal projections in the hollow tube shank and having a forward capturing tip of frustoconical shape matching the coupling nipple of the needle, the hollow tube shank having at least one orifice providing fluid communication between the plug and the hollow shank exterior, and elastic means linking the plug and the piston and placed in tension in a position of maximum compression of the annular elastomer washer.

2. A disposable syringe with an automatically retractable hypodermic needle as claimed in claim 1, wherein the coupling end of the outer tube includes an internal stop and internal retaining tongues spaced by an axial distance outwardly from the internal stop, and wherein the needle holder has an outer perimetral step of an axial length equivalent to the axial distance spacing between the internal stop and the internal retaining tongues.

3. A disposable syringe with an automatically retractable hypodermic needle as claimed in claim 1, wherein the distal guide conduit has a transverse elastic absorbent membrane.

4. A disposable syringe with an automatically retractable hypodermic needle as claimed in claim 1, wherein the capturing tip of the plug has an outer surface scored by a plurality of longitudinal grooves.

5. A disposable syringe with an automatically retractable hypodermic needle as claimed in claim 1, wherein the needle holder has at least one elastic retaining tongue at a posterior edge opposite an opening edge of the coupling nipple.

6. A disposable syringe with an automatically retractable hypodermic needle as claimed in claim 1, wherein the needle holder is an integral part of the forward housing of the outer tube.

7. A disposable syringe having an automatically retractable hypodermic needle as claimed in claim 1, having a circular transverse cross section and the hypodermic needle located centrally.

8. A disposable syringe having an automatically retractable hypodermic needle as claimed in claim 1, having a circular transverse cross section and the hypodermic needle located eccentrically, and including longitudinal guide means extending from the piston to the outer tube and another longitudinal guide means extending from the outer tube to the piston.

9. A disposable syringe with an automatically retractable hypodermic needle as claimed in claim 1, having an elliptical transverse cross section and the hypodermic needle located centrally.

10. A disposable syringe with an automatically retractable hypodermic needle as claimed in claim 1, having an elliptical transverse cross section and the hypodermic needle located eccentrically.

11. A disposable syringe with an automatically retractable hypodermic needle as claimed in claim 1, having an elliptical transverse cross section and a concavity in one of the major dimensions.

* * * * *